US011547856B2

(12) United States Patent
Salvia et al.

(10) Patent No.: US 11,547,856 B2
(45) Date of Patent: Jan. 10, 2023

(54) DIFFERENTIAL CHARGE-BALANCING DURING HIGH-FREQUENCY NEURAL STIMULATION

(71) Applicant: Verily Life Sciences LLC, South San Francisco, CA (US)

(72) Inventors: James Salvia, Belmont, CA (US); Meisam Heidarpour Roshan, Sunnyvale, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 188 days.

(21) Appl. No.: 16/566,025

(22) Filed: Sep. 10, 2019

(65) Prior Publication Data
US 2020/0078592 A1 Mar. 12, 2020

Related U.S. Application Data

(60) Provisional application No. 62/729,479, filed on Sep. 11, 2018.

(51) Int. Cl.
*A61N 1/36* (2006.01)
*A61N 1/06* (2006.01)
*A61N 1/02* (2006.01)

(52) U.S. Cl.
CPC .......... *A61N 1/36171* (2013.01); *A61N 1/06* (2013.01); *A61N 1/36153* (2013.01);
(Continued)

(58) Field of Classification Search
CPC ............ A61N 1/36125; A61N 1/36142; A61N 1/36146; A61N 1/3615; A61N 1/36153; A61N 1/36157
See application file for complete search history.

(56) References Cited

U.S. PATENT DOCUMENTS 5,573,550 A * 11/1996 Zadeh .................. A61N 1/3704
607/28
2006/0173493 A1 * 8/2006 Armstrong ......... A61N 1/36157
607/45
(Continued)

FOREIGN PATENT DOCUMENTS

| CN | 204840670 | 12/2015 |
| EP | 2374499 | 10/2011 |
| EP | 2374502 | 10/2011 |

OTHER PUBLICATIONS

International Application No. PCT/US2019/050350, "International Search Report and Written Opinion", dated Nov. 20, 2019, 24 pages.

*Primary Examiner* — Allen Porter
(74) *Attorney, Agent, or Firm* — Kilpatrick Townsend & Stockton LLP

(57) ABSTRACT

Differential charge-balancing can be used in high-frequency neural stimulation. For example, a neural stimulation apparatus can have first and second electrodes configured to be coupled proximate to a nerve fiber to implement a neural stimulation procedure. A neural stimulation circuit can be electrically coupled to the first and second electrodes. The neural stimulation circuit can apply stimulation currents to the nerve fiber through the first and second electrodes during a first stimulation phase of the neural stimulation procedure. The neural stimulation circuit can also apply a modified stimulation current to the nerve fiber through the first electrode during a second stimulation phase of the neural stimulation procedure. The modified stimulation current can be generated based on a difference between (i) a voltage at the first electrode, and (ii) a reference voltage derived from voltages on the first and second electrodes.

19 Claims, 8 Drawing Sheets

(52) U.S. Cl.
CPC .......... *A61N 1/36157* (2013.01); *A61N 1/025* (2013.01); *A61N 1/36064* (2013.01); *A61N 1/36096* (2013.01); *A61N 1/36103* (2013.01); *A61N 1/36125* (2013.01)

(56) References Cited

U.S. PATENT DOCUMENTS

| | | |
|---|---|---|
| 2012/0259382 A1 | 10/2012 | Trier et al. |
| 2017/0001003 A1* | 1/2017 | Pivonka ............. A61N 1/36007 |
| 2018/0133482 A1 | 5/2018 | Zou et al. |
| 2019/0255333 A1 | 8/2019 | Baru et al. |

* cited by examiner

DIFFERENTIAL CHARGE-BALANCING DURING HIGH-FREQUENCY NEURAL STIMULATION

CROSS-REFERENCE TO RELATED APPLICATIONS

The present application claims priority to Provisional Application No. 62/729,479, filed on Sep. 11, 2018, and entitled "Differential Charge-Balancing During High-Frequency Neural Stimulation," the entirety of which is hereby incorporated by reference herein.

TECHNICAL FIELD

The present disclosure relates generally to electrical therapeutic systems. More specifically, but not by way of limitation, this disclosure relates differential charge-balancing during high-frequency neural stimulation.

BACKGROUND

Many chronic diseases, such as epilepsy and depression, can be treated by stimulating the nerves in a patient's body using electrical signals. While such neural stimulation procedures are typically implemented using electrical signals with lower frequencies, e.g., 20 hertz (Hz) to 1 kHz, recent studies show that some diseases may be treatable using electrical signals with higher frequencies, e.g., from 1 kHz to 50 kHz.

SUMMARY

One example of the present disclosure includes a system comprising a set of electrodes configured to be coupled to a nerve fiber to implement a neural stimulation procedure. The system also comprises a stimulation circuit electrically coupled to the set of electrodes. The stimulation circuit is configured to apply stimulation currents through the set of electrodes to the nerve fiber during a stimulation phase of a treatment cycle in the neural stimulation procedure. The stimulation circuit is also configured to apply recovery currents through the set of electrodes to the nerve fibers during a recovery phase that is subsequent to the stimulation phase in the treatment cycle, the recovery currents having opposite polarities to the respective stimulation currents. The stimulation circuit is also configured to adjust one or more characteristics of the stimulation currents or the recovery currents based on a reference voltage derived from voltages on the set of electrodes, the one or more characteristics of the stimulation currents or the recovery currents being adjusted to reduce a charge buildup on the set of electrodes resulting at least partially from the stimulation phase and the recovery phase. The stimulation circuit is also configured to apply the stimulation currents or the recovery currents with the adjusted one or more characteristics through the set of electrodes to the nerve fiber during a subsequent treatment cycle of the neural stimulation procedure to reduce the charge buildup.

Another example of the present disclosure includes a method comprising applying stimulation currents through a set of electrodes to a nerve fiber during a stimulation phase of a treatment cycle in a neural stimulation procedure. The method also comprises applying recovery currents through the set of electrodes to the nerve fibers during a recovery phase that is subsequent to the stimulation phase in the treatment cycle, the recovery currents having opposite polarities to the respective stimulation currents. The method also comprises adjusting one or more characteristics of the stimulation currents or the recovery currents based on a reference voltage derived from voltages on the set of electrodes, the one or more characteristics of the stimulation currents or the recovery currents being adjusted to reduce a charge buildup on the set of electrodes resulting at least partially from the stimulation phase and the recovery phase. The method also comprises applying the stimulation currents or the recovery currents with the adjusted one or more characteristics through the set of electrodes to the nerve fiber during a subsequent treatment cycle of the neural stimulation procedure to reduce the charge buildup. Some or all of these steps can be performed by a neural stimulation device.

Still another example of the present disclosure includes a neural stimulation apparatus comprising a first electrode and a second electrode configured to be coupled proximate to a nerve fiber to implement a neural stimulation procedure. The neural stimulation apparatus also comprises a neural stimulation circuit electrically coupled to the first electrode and the second electrode. The neural stimulation circuit is configured to apply stimulation currents to the nerve fiber through the first electrode and the second electrode during a first stimulation phase of the neural stimulation procedure. The neural stimulation circuit is also configured to apply a modified stimulation current to the nerve fiber through the first electrode during a second stimulation phase of the neural stimulation procedure, wherein the modified stimulation current is generated based on a difference between (i) a voltage at the first electrode, and (ii) a reference voltage derived from voltages on the first electrode and the second electrode (e.g., as a result of the first stimulation phase).

Yet another example of the present disclosure includes a method comprising applying stimulation currents to a nerve fiber through a first electrode and a second electrode during a first stimulation phase of a neural stimulation procedure. The method also comprises applying a modified stimulation current to the nerve fiber through the first electrode during a second stimulation phase of the neural stimulation procedure, wherein the modified stimulation current is generated based on a difference between (i) a voltage at the first electrode, and (ii) a reference voltage derived from voltages on the first electrode and the second electrode (e.g., as a result of the first stimulation phase). Some or all of these steps can be performed by a neural stimulation apparatus.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

DETAILED DESCRIPTION

Figure 1:
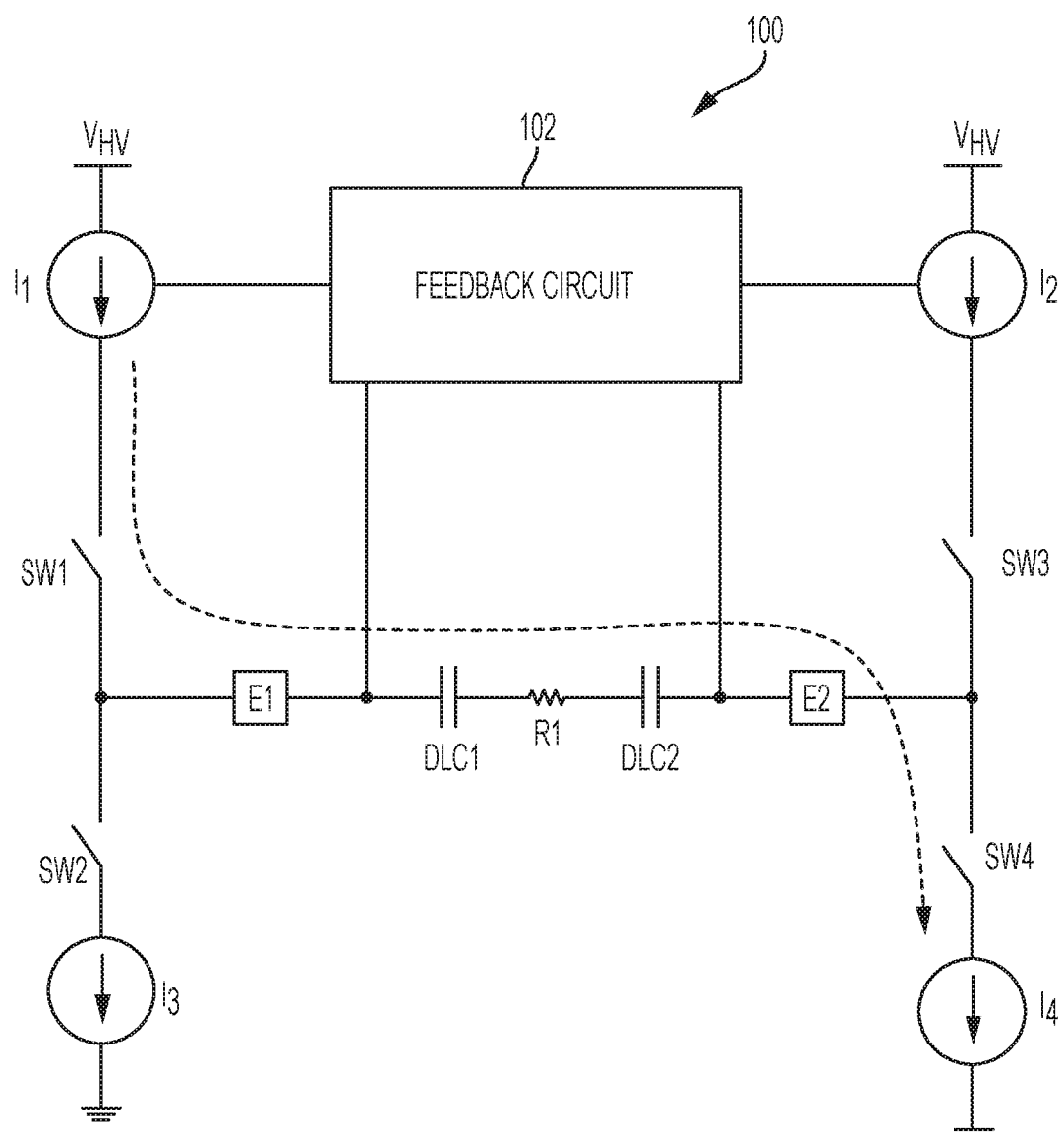
FIG. 1 is a circuit diagram of an example of a neural stimulation device according to some aspects of the present disclosure.

Reference will now be made in detail to various and alternative illustrative examples and to the accompanying drawings. Each example is provided by way of explanation and not as a limitation. It will be apparent to those skilled in the art that modifications and variations may be made. For instance, features illustrated or described as part of one example may be used in another example to yield a still further example. Thus, it is intended that this disclosure includes modifications and variations as come within the scope of the appended claims and their equivalents.

Illustrative Example of Providing Differential Charge-Balancing During Neural Stimulation One illustrative example of the present disclosure includes a neural stimulation device for applying high-frequency neural stimulation to a patient. The neural stimulation device includes a neural stimulation circuit coupled to a first electrode and a second electrode. The electrodes can be coupled to a nerve fiber in the patient's body, such as a nerve fiber in the patient's arm. The neural stimulation device can use the neural stimulation circuit to repeatedly apply current to the nerve fiber (via the electrodes) in a series treatment cycles, which collectively form a neural stimulation procedure.

Each of the treatment cycles can include a series of phases (e.g., stages). In the illustrative example, the phases include a stimulation phase and a recovery phase. During the stimulation phase, the neural stimulation device can apply a stimulation current having a certain polarity through the electrodes to the nerve fiber in order to stimulate the nerve. But repeatedly applying the stimulation current to the nerve fiber can cause charge to build up on the electrodes, which can potentially damage the nerve fiber. So, the neural stimulation device can next implement a recovery phase to reduce the charge build-up on the electrodes. During the recovery phase, the neural stimulation device can apply a recovery current through the electrodes to the nerve fiber. The recovery current can have a similar waveform but an opposite polarity to the stimulation current. The goal of the recovery phase is to entirely offset the charge build-up on the electrodes from the stimulation phase and return them to their normal state, but the recovery current is often not a perfect inverse replica of the stimulation current due to practical inefficiencies. As a result, a residual charge is often left over on the electrodes after the recovery phase. And if the stimulation and recovery phases are quickly repeated during several treatment cycles of a high-frequency neural stimulation procedure, the residual charge on the electrodes can rapidly build up to dangerous levels (e.g., greater than 0.5 v) at which chemical reactions can occur that damage the nerve fibers and the surrounding tissue.

To reduce or eliminate these dangers, in the illustrative example, the neural stimulation device can also implement a sampling phase. The sampling phase can occur after the recovery phase in each treatment cycle of the neural stimulation procedure. During the sampling phase, the neural stimulation device can derive a reference voltage from the voltages on the first and second electrodes. Specifically, the residual charge resulting from the stimulation and recovery phases can manifest as different voltages on the different electrodes. The neural stimulation device can derive a reference value from those voltages. Examples of the reference voltage can include an average of the voltages, a combination of the voltages, an aggregation of the voltages, a difference between the voltages, etc. After deriving the reference voltage, in some examples, the neural stimulation device can use the reference voltage to adjust one or more characteristics (e.g., an amplitude, frequency, wave shape, and/or duration) of the stimulation currents applied to the electrodes during the next stimulation phase of the next treatment cycle. For example, the neural stimulation device can include a feedback loop in which the difference between each electrode's voltage and the reference voltage is used to adjust the stimulation current driving the electrode during the next stimulation phase of the next treatment cycle. Additionally or alternatively, the neural stimulation device can use the reference voltage to adjust one or more characteristics of the recovery currents applied to the electrodes during the next recovery phase of the next treatment cycle. For example, the feedback loop can use the difference between each electrode's voltage and the reference voltage to adjust the recovery current driving the electrode during the next recovery phase of the next treatment cycle. In this way, the stimulation and/or recovery currents can be adjusted differentially during each treatment cycle to prevent the electrodes from building up dangerous levels of residual charge over the course several treatment cycles, without reducing the total amount of stimulation current and/or recovery current supplied to the patient during the neural stimulation procedure.

While the above example involves two electrodes for simplicity, other examples can involve more electrodes. For instance, neural stimulation device can include five electrodes through which the neural stimulation device can apply five stimulation currents during the stimulation phase and five recovery currents during the recovery phase. During the sampling phase, the neural stimulation device can derive a reference voltage from the voltages on the five electrodes, and then use the difference between each electrode's voltage and the reference voltage to adjust the stimulation current and/or recovery current driving the electrodes during the next treatment cycle.

The description of the illustrative example above is provided merely as an example, not to limit or define the limits of the present subject matter. Various other examples are described herein and variations of such examples would be understood by one of skill in the art. Advantages offered by various examples may be further understood by examining this specification and/or by practicing one or more examples of the claimed subject matter.

Illustrative Systems and Methods for Providing Differential Charge-Balancing During High-Frequency Neural Stimulation FIG. 1 is a circuit diagram of an example of a neural stimulation circuit 100 according to some aspects of the present disclosure. The neural stimulation circuit 100 can be used during a neural stimulation procedure, such as neuromodulation therapy, to treat a chronic disease. During the neural stimulation procedure, current sources I1-I2 deliver electrical current to a nerve fiber within a patient's tissue (represented by impedance R1 in FIG. 1) through electrodes E1-E2 positioned on or within the patient's tissue.

As the current flows through the electrodes E1-E2 to the patient's tissue, a double-layer capacitance may form at the interfaces between the electrodes E1-E2 and the tissue. For example, if the voltage across electrode E1 and the tissue is small (e.g., less than 0.5 v), then capacitance DLC1 is generated. And if the voltage across electrode E2 and the tissue is small, then capacitance DLC2 is also generated, thereby yielding a double-layer capacitance formed from DLC1 and DLC2. But if the voltage across one or both of these interfaces is large (e.g., greater than 0.5 v), then undesirable chemical reactions can occur that create a direct current (DC) path between the electrodes E1-E2, which can damage the tissue.

One way that the voltages across these interfaces can become dangerously large is through charge buildup on the electrodes E1-E2. Charge buildup can occur when the neural stimulation circuit 100 implements multiple treatment cycles of a neural stimulation procedure. Each treatment cycle can involve a stimulation phase. During the stimulation phase, the neural stimulation circuit 100 can close switches SW1 and SW4, while leaving switches SW2 and SW3 open. Examples of a switch can include a transistor, relay, or single-pole single-throw switch. With the switches in the above-described configuration, current can then flow from the current source I1 to electrode E1, through the tissue to electrode E2, and then to current source I4, as shown by the dashed line. Each treatment cycle can also include a recovery phase, which can occur after the stimulation phase. During the recovery phase, the neural stimulation circuit 100 can close switches SW3 and SW2, while leaving switches SW1 and SE4 open. Current can then flow from the current source I2 to electrode E2, through the tissue to electrode E1, and then to current source I3, in the direction opposite to the dashed line. After the stimulation phase and the recovery phase, some residual charge typically remains on the electrodes E1-E2. If the residual charge is not reduced or eliminated, the voltages on the electrodes E1-E2 can build up to dangerous levels after multiple treatment cycles.

To avoid these dangers, some examples of the present disclosure include a feedback circuit 102. The neural stimulation circuit 100 can activate the feedback circuit 102 during a sampling phase that occurs after the recovery phase. The feedback circuit 102 is an active circuit that uses a reference voltage derived from voltages on the electrodes E1-E2 to adjust the stimulation currents and/or recovery currents applied by the current sources I1-I2 during a subsequent treatment cycle. This is described in greater detail below with respect to FIG. 2.

Figure 2:
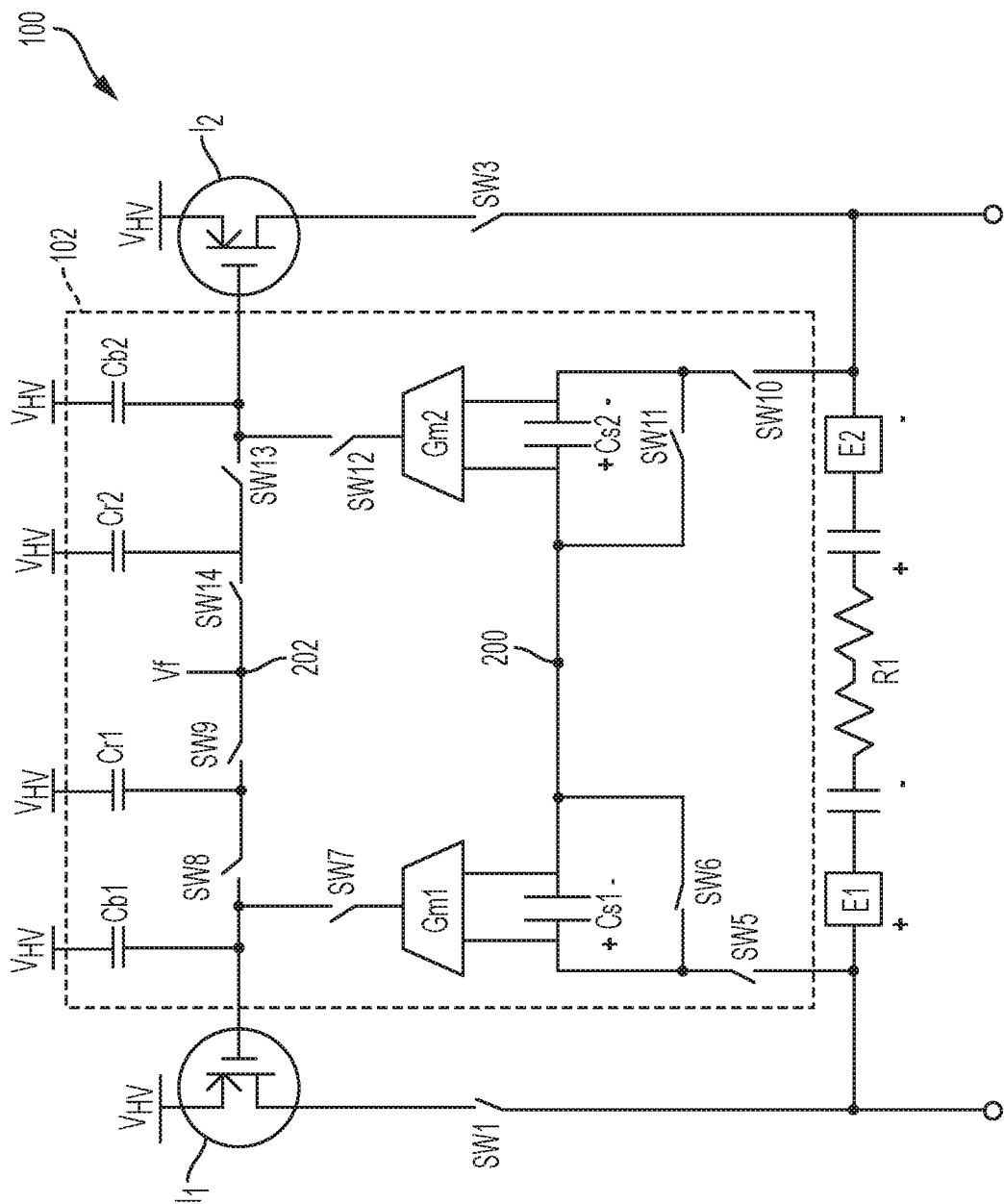
FIG. 2 is a circuit diagram showing a more detailed example of the neural stimulation device of FIG. 1 according to some aspects.

FIG. 2 shows a more detailed example of the upper half of the neural stimulation circuit 100 of FIG. 1 according to some aspects. As shown in FIG. 2, the feedback circuit 102 can generally include two halves corresponding to the two electrodes E1-E2. The left half can correspond to electrode E1 and can include switches SW5-SW9; capacitors Cs1, Cr1 and Cb1; and voltage-to-current converter Gm1. The left half can feed an electrical signal back to a transistor of the current source I1 to adjust stimulation and/or recovery currents provided by current source I1. The right half can correspond to electrode E2 and can include switches SW10-SE14; capacitors Cs2, Cr2, and Cb2; and voltage-to-current converter Gm2. The right half can feed an electrical signal back to a transistor of the current source I2 to adjust stimulation and/or recovery currents provided by current source I2. The two halves meet in the middle at common nodes 200 and 202. Operation of the neural stimulation circuit 100 with the feedback circuit 102 is discussed below with respect to FIGS. 3-5.

Figure 3:
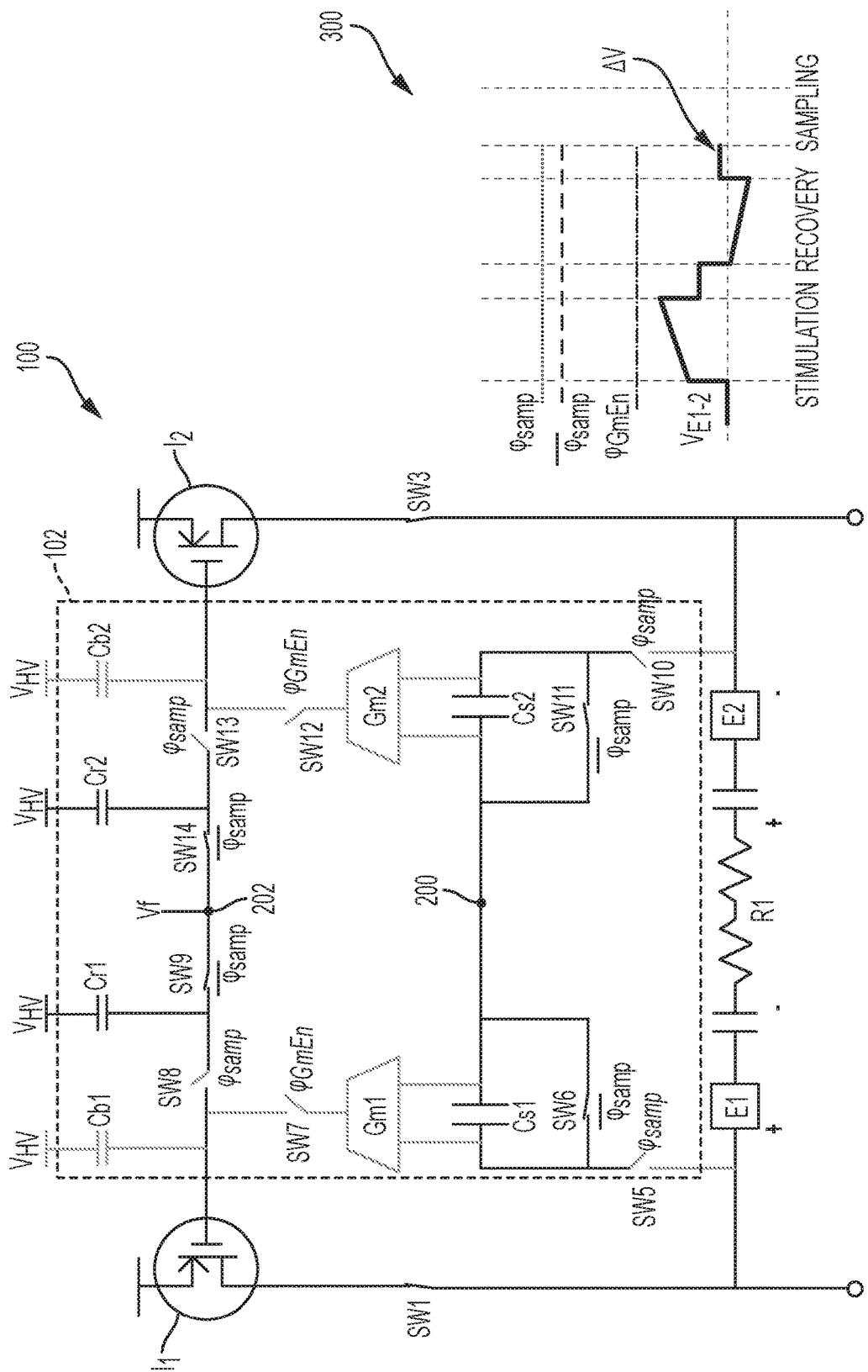
FIG. 3 is a circuit diagram showing an example of the neural stimulation device of FIG. 2 during the stimulation and recovery phases of a neural stimulation procedure according to some aspects.

FIG. 3 shows an example of the upper half of the neural stimulation circuit 100 during the stimulation and recovery phases of a neural stimulation procedure. Although not shown in FIG. 3 for simplicity, a control element (e.g., one or more processors, timers, and/or crystals) can be coupled to any combination of the switches SW1-SW12. The control element can transmit control signals to the switches SW1-SW12 in order to change their states and thereby implement the various phases of a treatment cycle. For example, the control element can initiate a stimulation phase by transmitting a close signal (e.g., a high signal) configured to cause the switch SW1 to close and an open signal (e.g., a low signal) configured to cause the switch SW3 to open. When the switches SW1, SW3 are in these states, a stimulation current can flow from the current source I1 through electrodes E1-E2, thereby stimulating the patient's tissue and generating a positive voltage across the electrodes E1-E2. An example of this positive voltage during the stimulation phase is shown by line $V_{E1\text{-}2}$ in the graph 300. Once the stimulation phase is complete, the control element can initiate a recovery phase by transmitting an open signal configured to cause the switch SW1 to open and a close signal configured to cause the switch SW3 to close. When the switches SW3, SW1 are in these states, a recovery current can flow in the opposite direction from the current source I2 through electrodes E1-E2, thereby generating a negative voltage across the electrodes E1-E2. An example of this negative voltage during the recovery phase is shown by line $V_{E1\text{-}2}$ in the graph 300. At the end of the recovery phase, a residual charge ($\Delta V$) remains on the electrodes.

During the stimulation and recovery phases, the components of the feedback circuit 102 shown using darker colors in FIG. 3 are active, while the components of the feedback circuit 102 shown in lighter colors in FIG. 3 are inactive. For example, during both of these phases, the control element can open switches SW5 and SW10 to prevent current flow to the feedback circuit 102. The control element can also close the switches SW6 and SW11 to reset the sampling capacitors Cs1-Cs2. Additionally, the control element can open the switches SW8 and SW13 to prevent current flow from reference capacitors Cr1-Cr2 to the current sources I1-I2, and close switches SW9 and SW14 to enable reference capacitors Cr1-Cr2 to charge to the fixed voltage (Vf) at the common node 202.

Figure 4:
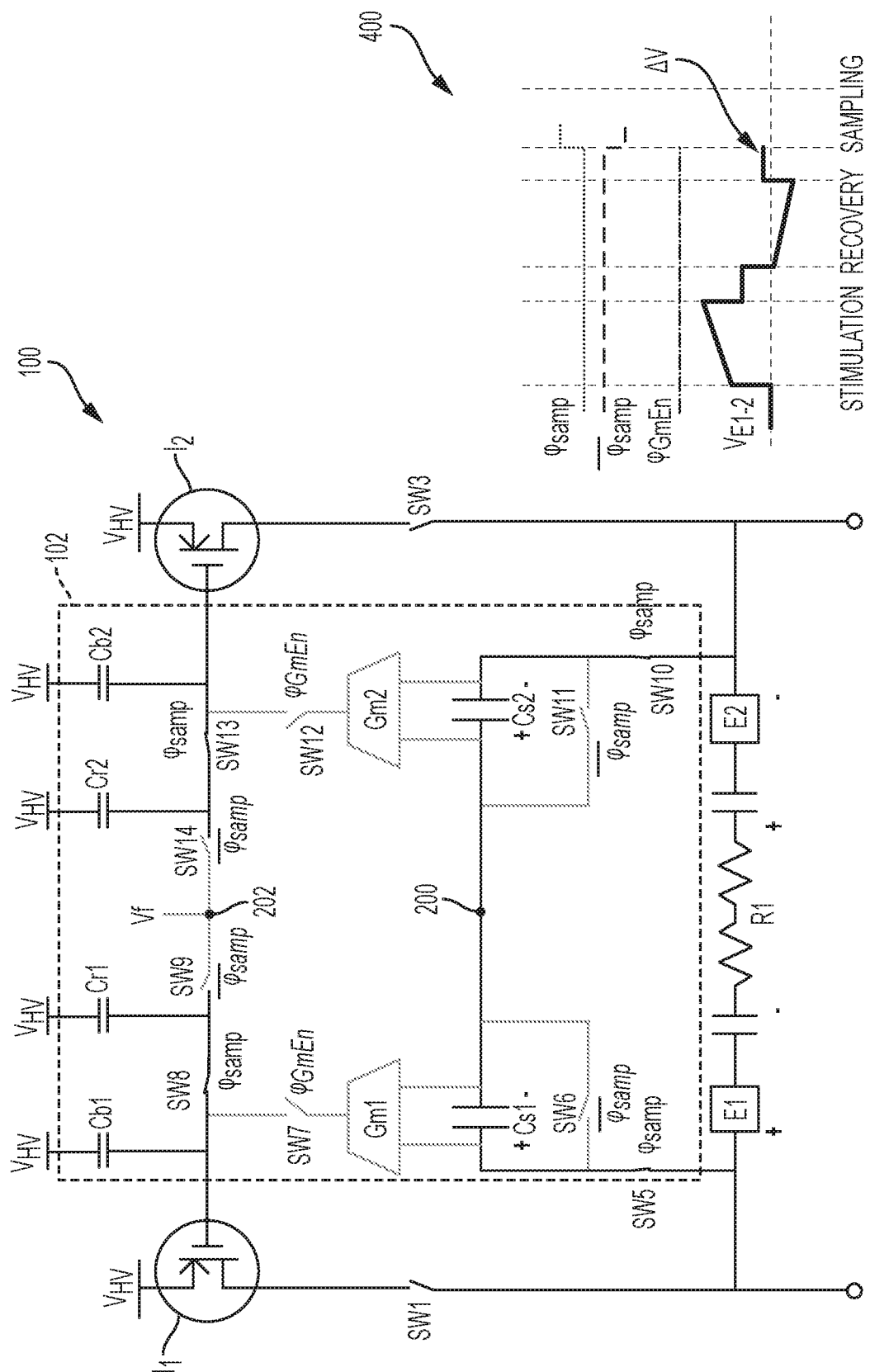
FIG. 4 is a circuit diagram showing an example of the neural stimulation device of FIG. 2 during a sampling phase of a neural stimulation procedure according to some aspects.
Figure 5:
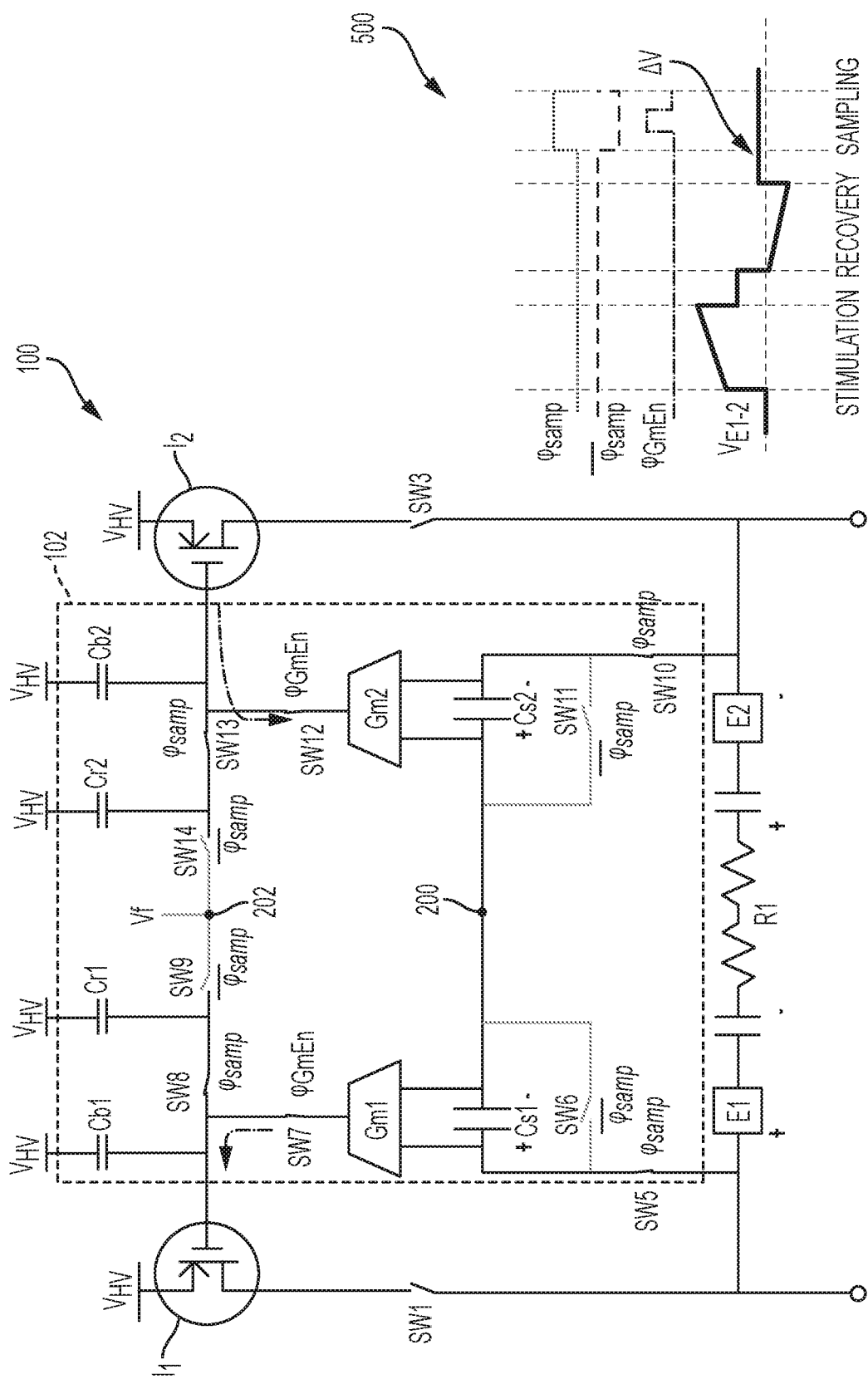
FIG. 5 is a circuit diagram showing another example of the neural stimulation device of FIG. 2 during a sampling phase of a neural stimulation procedure according to some aspects.

After the recovery phase, the control element can initiate the sampling phase by transmitting open signals configured to cause some or all of the switches SW1-SW4 to open, for example, as shown in FIGS. 4-5. In those figures, the components of the feedback circuit 102 shown using darker colors in FIGS. 4-5 are active, while the components of the feedback circuit 102 shown in lighter colors in FIGS. 4-5 are inactive.

Referring now to FIG. 4, during the sampling phase, the control element can transmit close signals to switches SW5, SW8, SW10, and SW13 to close those switches. An example of such a close signal is represented by $\phi_{samp}$ in graph 400. And the control element can also transmit open signals to switches SW6, SW9, SW11, and SW14 to open those switches. An example of such an open signal is represented by $\overline{\phi}_{samp}$ in graph 400. When the feedback circuit 102 is in this switch configuration, the sampling capacitors Cs1-Cs2 can generate the reference voltage (e.g., an average voltage) between the electrodes E1-E2 at the common node 200. The sampling capacitors Cs1-Cs2 can also each charge to a voltage level that is the difference between each electrode's voltage and the reference voltage at node 200. For example, sampling capacitor Cs1 can charge to a voltage level that is the difference between the voltage at electrode E1 and the reference voltage at the common node 200. And sampling capacitor Cs2 can charge to a voltage level that is the difference between the voltage at electrode E2 and the reference voltage at the common node 200. This process can be referred to as sampling, whereby the sampling capacitors Cs1-Cs2 are sampling the differences between each electrode's voltage and the reference voltage at the common node 200.

During the sampling phase, the control element can further activate the voltage-to-current converters Gm1-Gm2 for a brief time period, as shown in FIG. 5. Referring to FIG. 5, the control element can transmit close signals to switches SW7 and SW12 to close those switches. An example of such a close signal is represented by $\phi_{GmEn}$ in graph 500. With switch SW7 closed, the voltage-to-current converter Gm1 can generate a first signal (e.g., an output current) that is related to the voltage across the sampling capacitor Cs1. Since the voltage across the sampling capacitor Cs1 is the difference between the reference voltage at the common node 200 and the voltage at electrode E1, the first signal from the voltage-to-current converter Gm1 can be related to the difference between the reference voltage at the common node 200 and the voltage at electrode E1. The voltage-to-current converter Gm1 can transmit the first signal toward a terminal (e.g., gate) of the current source I1, as shown by a dashed arrow in FIG. 5. The first signal can combine with another signal (e.g., a fixed current) from the reference capacitor Cr1 to arrive at a combined signal that is fed back to the current source I1. Providing the combined signal to the current source I1 can cause the current source I1 to adjust a characteristic of the stimulation current applied to electrode E1 during a subsequent stimulation phase and/or the recovery current applied to electrode E1 during a subsequent recovery phase.

Similarly to the above, with switch SW12 closed, the voltage-to-current converter Gm2 can generate a second signal that is related to (e.g., proportional to) the voltage across the sampling capacitor Cs2. Since the voltage across the sampling capacitor Cs2 is the difference between the reference voltage at the common node 200 and the voltage at electrode E2, the second signal from the voltage-to-current converter Gm2 can be related to the difference between the reference voltage at the common node 200 and the voltage at electrode E2. The voltage-to-current converter Gm2 can transmit the second signal toward a terminal of the current source I2. The second signal can combine with another signal from the capacitor Cr2 to arrive at a combined signal that is fed back to the current source I2. Providing the combined signal to the current source I2 can cause the current source I2 to adjust a characteristic of the stimulation current applied to electrode E2 during a subsequent stimulation phase and/or the recovery current applied to electrode E2 during a subsequent recovery phase.

Figure 6:
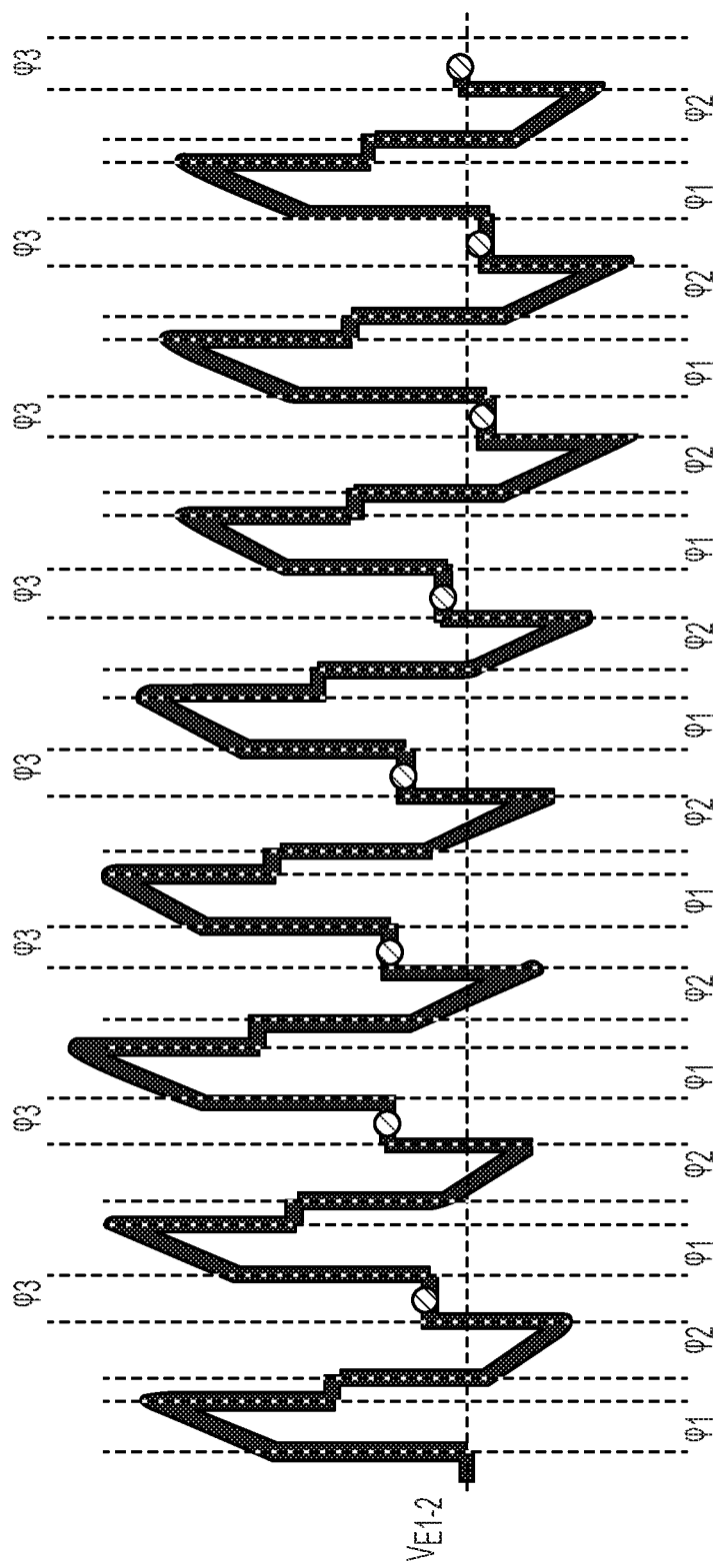
FIG. 6 is a graph of an example of voltages across electrodes over the course of several treatment cycles during a neural stimulation procedure according to some aspects.

The adjustments to the stimulation and/or recovery currents may be slight in order to incrementally reduce the residual voltage on the electrodes E1-E2 to zero over several treatment cycles. One example of this process is shown in FIG. 6. FIG. 6 depicts eight treatment cycles, though any number of treatment cycles is possible. Each treatment cycle includes a stimulation phase ($\phi_1$), a recovery phase ($\phi_2$), and a sampling phase ($\phi_3$). Over the course of the treatment cycles, each of these phases is applied periodically. As a result, the residual voltage on electrodes E1-E2 is gradually adjusted such that it oscillates around and ultimately reduces to approximately zero.

While the examples shown in FIGS. 2-5 depict two electrodes with corresponding feedback components, the neural stimulation circuit 100 can include any number and combination of electrodes with corresponding current sources and feedback components. As one such example, the neural stimulation circuit 100 can include a third current source coupled to a third electrode (e.g., E3) to deliver stimulation and recovery currents to the patient's tissue via the third electrode. The neural stimulation circuit 100 can also include feedback components coupled between the third current source and the third electrode, whereby the feedback components can be configured in any of the arrangements discussed above. For example, the feedback components can include a sampling capacitor (e.g., Cs3), a voltage-to-current converter (e.g., Gm3), a reference capacitor (e.g., Cr3), another capacitor (e.g., Cb3), and various switches. These components can be configured as shown in FIGS. 2-5, with a lead of the sampling capacitor coupled to the common node 200 to generate a reference voltage based on the voltages on electrodes E1-E3 at the common node 200, and a lead of the reference capacitor can be coupled to the common node 202 for charging to the fixed voltage Vf.

Further, while the feedback circuit 102 shown in FIGS. 2-5 has a certain arrangement of circuit components, other arrangements of circuit components are possible. Some examples can include more circuit components, fewer circuit components, different circuit components, or a different combination of the circuit components than are shown in FIGS. 2-5. For instance, some examples may use various digital components (e.g., logic gates, processors, analog-to-digital converters, or digital-to-analog converters) additionally or alternatively to the analog components depicted in FIGS. 2-5. In one such example, the feedback circuit 102 can include a processor additionally or alternatively to the voltage-to-current converters Gm1-Gm2. The processor can detect the voltage across the sampling capacitor Cs1 and responsively transmit a first signal to the current source I1 to adjust a first stimulation current that it applies during a subsequent stimulation phase and/or a first recovery current that it applies during a subsequent recovery phase. The processor can also detect the voltage across the sampling capacitor Cs2 and responsively transmit a second signal to the current source I2 to adjust a second stimulation current that it applies during a subsequent stimulation phase and/or a second recovery current that it applies during a subsequent recovery phase.

As another example, the feedback circuit 102 can include comparators additionally or alternatively to the voltage-to-current converters Gm1-Gm2 and/or the sampling capacitors Cs1-Cs2. The comparators can include a first comparator configured to compare the voltage on the electrode E1 to the reference voltage to determine if voltage on the electrode E1 is above or below the reference voltage. If the charge buildup on the electrode E1 is greater than the reference voltage, the first comparator can output a first signal (e.g., a current pulse) to the current source I1 to cause the current source I1 to adjust a first stimulation current that it applies during a subsequent stimulation phase and/or a first recovery current that it applies during a subsequent recovery phase. Likewise, the comparators can include a second comparator configured to compare the voltage on the electrode E2 to the reference voltage to determine if voltage on the electrode E2 is above or below the reference voltage. If the charge buildup on the electrode E2 is greater than the reference voltage, the second comparator can output a second signal to the current source I2 to cause the current source I2 to adjust a second stimulation current that it applies during a subsequent stimulation phase and/or a second recovery current that it applies during a subsequent recovery phase.

Figure 8:
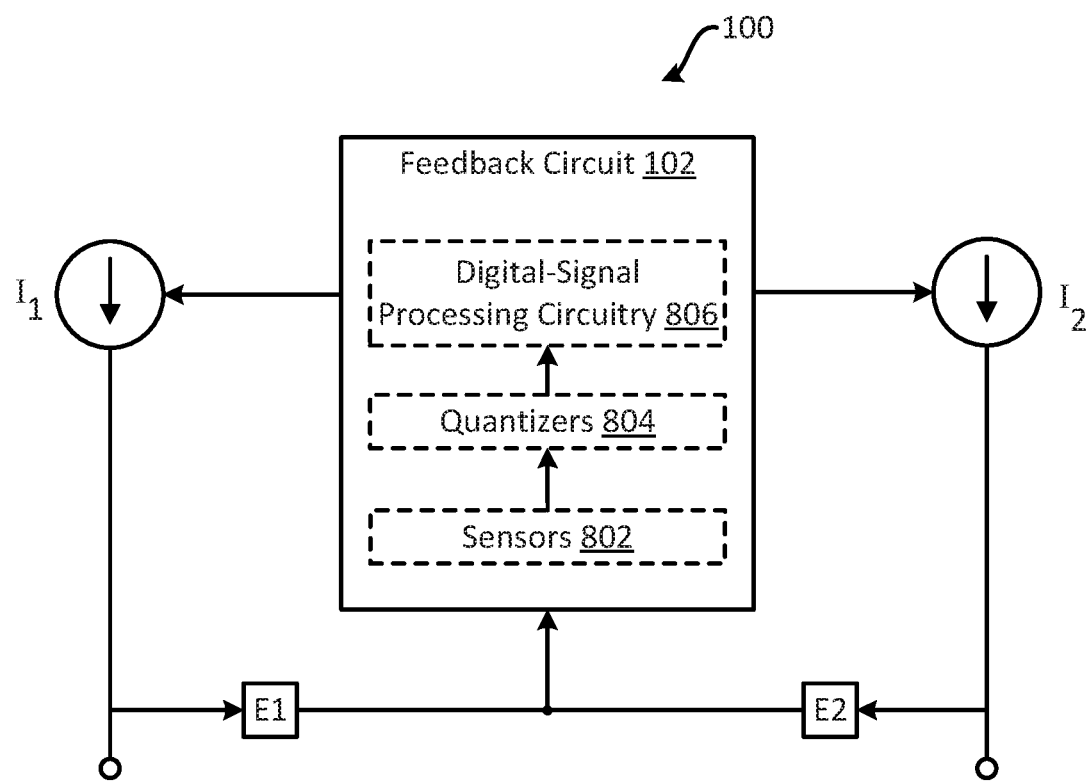
FIG. 8 is a block diagram of an example of the upper half of a neural stimulation device according to some aspects.

Yet another example that relies more heavily on digital circuitry is shown in FIG. 8, which depicts the upper half of a neural stimulation circuit 100 according to some aspects. The neural stimulation circuit 100 includes the feedback circuit 102. The feedback circuit 102 can detect a voltage associated with the electrodes E1-E2 and control the current sources I1-I2 to adjust the stimulation currents and/or the recovery currents that are subsequently applied.

More specifically, the feedback circuit 102 includes one or more sensors 802 configured to detect a voltage associated with the electrodes E1-E2. Examples of the sensors 802 can include a voltmeter or a capacitor, such as capacitor Cs1 of FIG. 2. The sensors 802 may detect a voltage at E1, a voltage at E2, a reference voltage, or any combination of these. The sensors 802 can output sensor signals indicative of the detected voltages. One or more quantizers 804 can receive the sensor signals from the sensors 802 and convert the voltages detected by the sensors 802 into digital signals. An example of a quantizer can include an analog-to-digital converter, such as a 5-bit analog-to-digital converter. The quantizers 804 can transmit the digital signals to digital-signal processing circuitry 806, which may include logic gates, such as AND, OR, NOT, and NAND gates; processors, such as proportional integral controllers; integrated circuit (IC) components, such as amplifiers or comparators; or any combination of these. The digital-signal processing circuitry 806 can receive the digital signals and generate first and second signals based on the digital signals. The digital-signal processing circuitry 806 can then transmit the first and second signals to the current sources I1-I2, respectively, to control the current sources I1-I2 (e.g., to adjust the stimulation currents and/or recovery currents that are subsequently applied).

In some examples, the quantizers 804 can include a quantizer that is dedicated to each electrode. So, if there are two electrodes (e.g., electrodes E1-E2), there will be two quantizers. And if there are three electrodes, there will be three quantizers. And so on. Each quantizer can receive an analog signal from the sensors 802, where the analog signal represents a voltage at the quantizer's corresponding electrode. Each quantizer can then generate a digital signal based on the analog signal and transmit the digital signal to the digital-signal processing circuitry 806, which in turn can process the digital signals to determine how to adjust the stimulation currents and/or recovery currents applied by the current sources I1-I2.

In other examples, the quantizers 804 can include a multi-channel quantizer. The multi-channel quantizer may have as many channels as there are electrodes. For example, the multi-channel quantizer can include a first channel corresponding to electrode E1 and a second channel corresponding to electrode E2. Each channel can receive an analog signal representing a voltage detected at its corresponding electrode. For example, the first channel can receive a first analog signal representing a first voltage detected at electrode E1, and the second channel can receive a second analog signal representing a second voltage detected at electrode E2. The multi-channel quantizer can generate one or more digital signals based on the received analog signals. For example, the multi-channel quantizer can generate a single digital signal based on the first analog signal associated with electrode E1 and the second analog signal associated with E2, where the single digital signal is representative of a difference between the first voltage at electrode E1 and the second voltage at electrode E2. The multi-channel quantizer can then transmit the digital signal (s) to the digital-signal processing circuitry 806.

The digital-signal processing circuitry 806 can receive the digital signal(s) from the quantizer(s) 804 and control the current sources I1-I2 based on the digital signal(s). For example, digital-signal processing circuitry 806 can determine a voltage at E1, a voltage at E2, a reference voltage (e.g., a difference between the voltages at E1-E2), or any combination of these, based on the digital signal(s). The digital-signal processing circuitry 806 can then control the current sources I1-I2 based on the determined voltage, so as to adjust the characteristics (e.g., amplitudes, pulse widths, or both) of the stimulation currents and/or recovery currents. This may reduce charge buildup.

As one specific example, the digital-signal processing circuitry 806 can include a proportional integral controller. The proportional integral controller can control the current sources I1-I2 based on the digital signal(s) received from the quantizer(s) 804, so as to adjust the characteristics of stimulation currents and/or recovery currents. For instance, the proportional integral controller can generate a first signal configured to increase an amount of current output by the current source I1 by a certain amount (e.g., +10 mA), and generate a second signal configured to decrease an amount of current output by the current source I2 by the same amount (e.g., −10 mA). This may result in the currents output by the current sources I1-I2 generally offsetting each other, which can reduce charge buildup.

While the example shown in FIG. 8 depicts two electrodes E1-E2, the neural stimulation circuit 100 can include any number and combination of electrodes with corresponding feedback components. Further, while the feedback circuit 102 shown in FIG. 8 has a certain arrangement of components, other examples can include more components, fewer components, different components, or a different arrangement of the components than are shown in FIG. 8. For instance, some examples may lack separate sensors 802 and instead rely on the quantizers 804 to serve as the sensors (e.g., to detect the voltage), since a quantizer can generally measure voltage directly. And some examples may involve the quantizers 804 being part of (e.g., internal to) a processor of the digital-signal processing circuitry 806. Further, any aspects discussed above in relation to FIG. 8 can be combined with any with aspects discussed above with respect to FIGS. 1-5 to yield still further examples.

Figure 7:
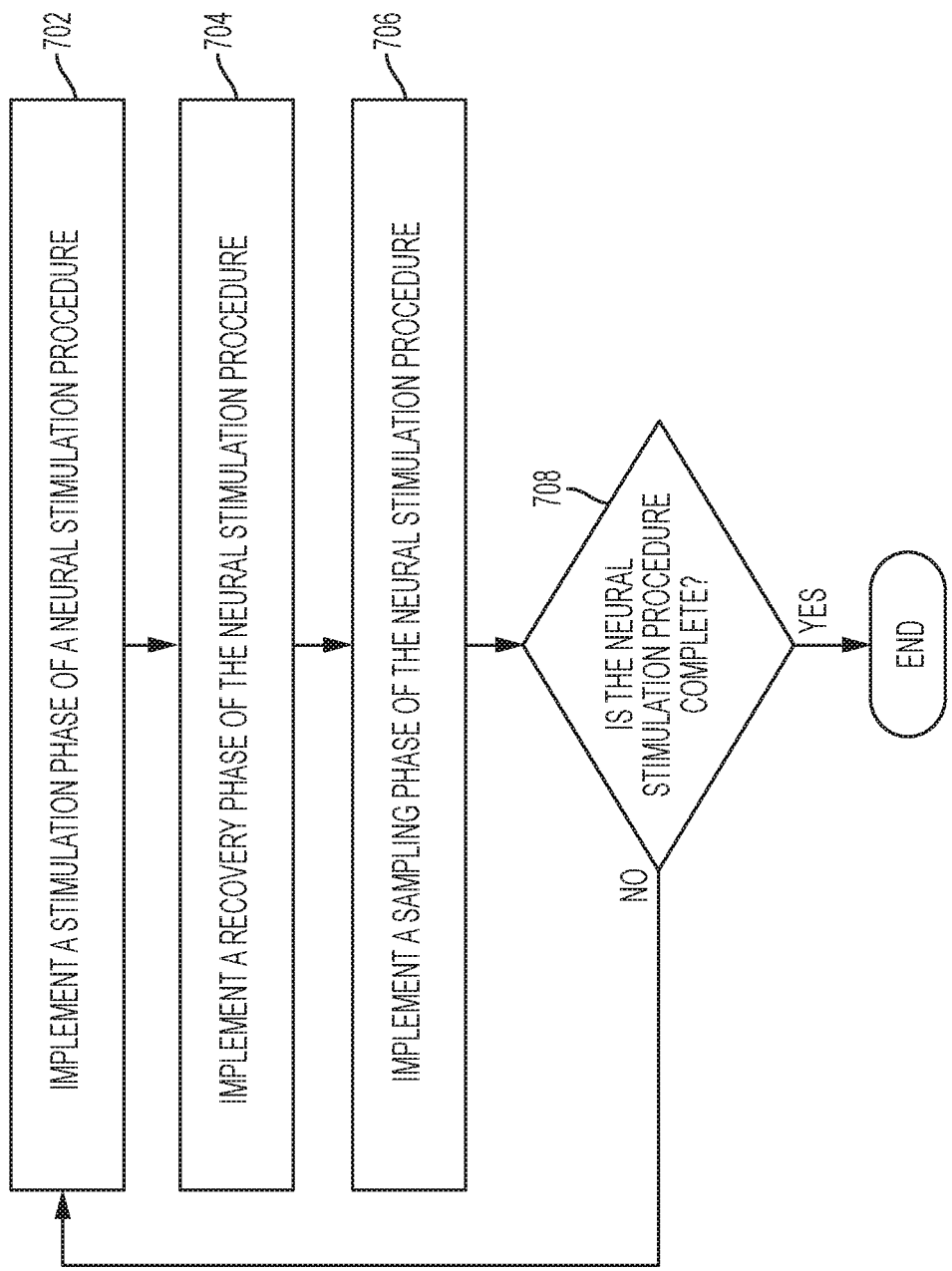
FIG. 7 is a flow chart of an example of a process for implementing a neural stimulation procedure according to some aspects.

FIG. 7 is a flow chart of an example of a process for implementing a neural stimulation procedure according to some aspects. Other examples can include more steps, fewer steps, different steps, or a different combination of steps than are shown in FIG. 7. The steps of FIG. 7 are discussed below with reference to the components discussed above in relation to FIGS. 2-5.

In block 702, a neural stimulation device uses a neural stimulation circuit 100 to implement a stimulation phase of a neural stimulation procedure. More specifically, the neural stimulation device initiates the stimulation phase by operating a control element, which transmits a close signal to switch SW1 and an open signal to switch SW3. The close signal causes switch SW1 to close and the open signal causes switch SW3 to open. Closing switch SW1 completes a circuit between the current source I1 and electrode E1, thereby enabling the current source I1 to transmit stimulation current to electrode E1, through a nerve fiber in the patient's tissue to electrode E2, and then towards ground. The stimulation current stimulates the nerve fiber in the patient's tissue as it passes between electrodes E1 and E2, but also leaves an electric charge on the electrodes E1-E2 as a result.

The amount of stimulation current transmitted to the nerve fiber can change depending on the treatment cycle. For example, during the first treatment cycle of the neural stimulation procedure, the current source I1 can be configured to transmit an initial amount of stimulation current to the nerve fiber. The initial amount of stimulation current can be set by an operator of the neural stimulation device (e.g., as part of the neural stimulation procedure). For example, the neural stimulation device can receive user input specifying the initial amount of stimulation current to be delivered to the nerve fiber during the first treatment cycle. In response to the user input, the neural stimulation device can configure the current source I1 to deliver that amount of stimulation current to the nerve fiber during the first treatment cycle. During subsequent cycles of the neural stimulation procedure, the amount of stimulation current delivered to the nerve fiber during the stimulation phase can be adjusted by the feedback circuit 102, for example, as discussed in greater detail below.

In block 704, the neural stimulation device uses the neural stimulation circuit 100 to implement a recovery phase of the neural stimulation procedure. More specifically, the neural stimulation device can end the stimulation phase and initiate the recovery phase by operating the control element such that the control element transmits an open signal to switch SW1 and a close signal to switch SW3. The open signal causes switch SW1 to open and the close signal causes switch SW3 to close. Closing switch SW3 completes a circuit between the current source I2 and electrode E2, thereby enabling the current source I2 to transmit a recovery current to electrode E2, through the nerve fiber in the patient's tissue to electrode E1, and then towards ground. This recovery current stimulates the nerve fiber as it passes between electrodes E1 and E2. Since the recovery current can have an opposite polarity to the stimulation current, the recovery current can reduce the amount of electric charge on the electrodes E1-E2. However, there may still be a residual charge leftover at the end of the recovery phase.

The amount of recovery current transmitted to the nerve fiber can change depending on the treatment cycle. For example, during the first treatment cycle of the neural stimulation procedure, the current source I2 can be configured to transmit an initial amount of recovery current to the nerve fiber. The initial amount of recovery current can be set by an operator of the neural stimulation device (e.g., as part of the neural stimulation procedure). For example, the neural stimulation device can receive user input specifying the initial amount of recovery current to be delivered to the nerve fiber during the first treatment cycle. In response to the user input, the neural stimulation device can configure the current source I2 to deliver that amount of recovery current to the nerve fiber during the first treatment cycle. During subsequent cycles of the neural stimulation procedure, the amount of recovery current delivered to the nerve fiber during the stimulation phase can be adjusted by the feedback circuit 102, for example, as discussed in greater detail below.

In block 706, the neural stimulation device uses the neural stimulation circuit 100 to implement a sampling phase of the neural stimulation procedure. More specifically, the neural stimulation device can end the recovery phase and initiate the sampling phase by operating the control element such that the control element transmits open signals to switches SW1 and SW3. The open signals cause the switches SW1 and SW3 to open, preventing current flow between the current sources I1-I2 and the electrodes E1-E2.

With switches SW1 and SW3 open, the control element can then implement the sampling phase by operating the switches SW5-SW14 (e.g., as discussed above) to generate first and second signals based on a reference voltage at common node 200. The feedback circuit 102 can supply the first and second signals to the current sources I1-I2, respectively, thereby causing the current sources I1-I2 to adjust respective characteristics of the stimulation currents in a subsequent stimulation phase and/or the recovery currents in a subsequent recovery phase.

As a particular example, the control element can close switches SW5 and SW10. Closing these switches electrically couples the first electrode E1 to the second electrode E2 at the common node 200, thereby producing the reference voltage at the common node 200. Closing these switches also causes the first sampling capacitor Cs1 to charge to a first voltage, whereby the first voltage represents a first voltage difference between the first electrode's voltage and the reference voltage. The voltage-to-current converters Gm1 can then detect the first voltage across the sampling capacitor Cs1 and generate the first signal based on the first voltage across the first sampling capacitor Cs1. Likewise, closing switches SW5 and SW10 causes the second sampling capacitor Cs2 to a second voltage, whereby the second voltage represents a second voltage difference between the second electrode's voltage and the reference voltage. The voltage-to-current converter Gm2 can detect the second voltage across the second sampling capacitor Cs2 and responsively generate the second signal based on the second voltage across the second sampling capacitor Cs2. The control element can then close switches SW7 and SW12, enabling the voltage-to-current converters Gm1-Gm2 to transmit the first and second signals towards the first and second current sources I1-I2, respectively.

In some examples, the first and second signals are relatively unadulterated before being fed back to the current sources I1-I2, while in other examples each of the first and second signals can be mixed with other signals (e.g., from reference capacitors Cr1-Cr2) before being fed back to the current sources I1-I2. Either way, the current sources I1-I2 can adjust one or more characteristics (e.g., an amplitude, frequency, waveform, and/or duration) of a stimulation current or a recovery current applied during a subsequent treatment cycle based on the first and second signals which, as discussed above, are themselves based on the reference voltage derived from the voltages on the set of electrodes E1-E2. The one or more characteristics stimulation currents and/or recovery currents can be adjusted to reduce a charge buildup on the set of electrodes E1-E2 resulting at least partially from the stimulation phase and the recovery phase.

In block 708, the neural stimulation device determines if the neural stimulation procedure is complete. For example, the neural stimulation device may be preprogrammed to implement a neural stimulation procedure with a particular number of treatment cycles, where each treatment cycle includes some or all of the steps shown in blocks 702-706. The neural stimulation procedure can use a counter to keep track of the number of treatment cycles already implemented for determining whether there the neural stimulation procedure is complete. If the neural stimulation procedure is complete, the process can end. Otherwise, the process can return to block 702 and iterate. For example, the process can return to block 702 where the neural stimulation device can use the neural stimulation circuit 100 to implement another stimulation phase, in which the neural stimulation circuit 100 applies stimulation currents and/or recovery currents with the adjusted one or more characteristics (e.g., as a result of the sampling phase in block 706) through the electrodes E1-E2 to the nerve fiber in order to reduce the charge buildup on the electrodes E1-E2.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure. For instance, any example(s) described herein can be combined with any other example(s).

The invention claimed is:

1. A method comprising:
applying, by a first current source of a neural stimulation device, stimulation currents through a set of electrodes to a nerve fiber during a stimulation phase of a treatment cycle in a neural stimulation procedure;
applying, by a second current source of the neural stimulation device, recovery currents through the set of electrodes to the nerve fibers during a recovery phase that is subsequent to the stimulation phase in the treatment cycle, the recovery currents having opposite polarities to the respective stimulation currents;
adjusting, by the neural stimulation device, one or more characteristics of the stimulation currents provided by the first current source or the recovery currents provided by the second current source based on a reference voltage derived from voltages on the set of electrodes, the one or more characteristics of the stimulation currents or the recovery currents being adjusted to reduce a charge buildup on the set of electrodes resulting at least partially from the stimulation phase and the recovery phase, wherein adjusting the one or more characteristics includes:
generating a signal based on a voltage across a sampling capacitor of the neural stimulation device, the voltage across the sampling capacitor being dependent on the reference voltage; and
supplying the signal to a current source electrically coupled to the set of electrodes, the current source being the first current source or the second current source, and the current source being configured to receive the signal and adjust the one or more characteristics based on the signal; and
applying, by the neural stimulation device, the stimulation currents or the recovery currents with the adjusted one or more characteristics through the set of electrodes to the nerve fiber during a subsequent treatment cycle of the neural stimulation procedure to reduce the charge buildup.

2. The method of claim 1, wherein:
the one or more characteristics includes at least one of an amplitude, a wave shape, or a duration; and
the reference voltage is an average voltage among the set of electrodes.

3. The method of claim 1, wherein the set of electrodes includes a first electrode and a second electrode, the first electrode being coupled to the second electrode at a common node to produce the reference voltage at the common node, and further comprising:
charging the sampling capacitor to the voltage, the sampling capacitor being electrically coupled between the common node and an electrode in the set of electrodes such that the voltage represents a voltage difference between the electrode's voltage and the reference voltage.

4. The method of claim 1, wherein:
the current source includes a transistor with a gate; and
supplying the signal to the current source involves supplying the signal to the gate of the transistor.

5. The method of claim 1, wherein:
the signal is generated by a voltage-to-current converter, the signal being a current that is proportional to the voltage across the sampling capacitor.

6. The method of claim 1, wherein:
the signal is generated by a comparator configured to compare a voltage on an electrode in the set of electrodes to the reference voltage.

7. The method of claim 1, wherein the one or more characteristics of the stimulation currents or the recovery currents are adjusted based on a difference between (i) a voltage at a first electrode in the set of electrodes, and (ii) the reference voltage derived from the voltages on the set of electrodes.

8. A system, comprising:
a set of electrodes configured to be coupled to a nerve fiber to implement a neural stimulation procedure; and
a stimulation circuit electrically coupled to the set of electrodes, the stimulation circuit being configured to:
apply stimulation currents from a first current source through the set of electrodes to the nerve fiber during a stimulation phase of a treatment cycle of the neural stimulation procedure;
apply recovery currents from a second current source through the set of electrodes to the nerve fibers during a recovery phase that is subsequent to the stimulation phase in the treatment cycle, the recovery currents having opposite polarities to the respective stimulation currents;
generate a signal based on a voltage across a sampling capacitor of the stimulation circuit, the voltage across the sampling capacitor being dependent on a reference voltage that is derived from voltages on the set of electrodes;
transmit the signal to a current source electrically coupled to the set of electrodes, the current source being the first current source or the second current source, and the current source being configured to receive the signal and responsively adjust one or more characteristics of the stimulation currents or the recovery currents based on the signal, the one or more characteristics of the stimulation currents or the recovery currents being adjusted to reduce a charge buildup on the set of electrodes resulting at least partially from the stimulation phase and the recovery phase; and
apply the stimulation currents or the recovery currents with the adjusted one or more characteristics through the set of electrodes to the nerve fiber during a subsequent treatment cycle of the neural stimulation procedure to reduce the charge buildup.

9. The system of claim 8, wherein the one or more characteristics includes at least one of an amplitude, a wave shape, or a duration.

10. The system of claim 8, wherein the set of electrodes includes a first electrode and a second electrode, wherein the stimulation circuit includes:
a first sampling capacitor;

a second sampling capacitor electrically coupled to the first sampling capacitor at a common node;

a first switch electrically coupled between the first sampling capacitor and the first electrode, the first switch being operable to electrically couple the first electrode to the common node through the first sampling capacitor; and a second switch electrically coupled between the second sampling capacitor and the second electrode, the second switch being operable to electrically couple the second electrode to the common node through the second sampling capacitor, wherein the sampling capacitor is the first sampling capacitor or the second sampling capacitor.

11. The system of claim 10, wherein the stimulation circuit is further configured to implement a sampling phase of the neural stimulation procedure that is subsequent to the recovery phase by:

operating the first switch and the second switch to electrically couple (i) the first electrode to the common node through the first sampling capacitor, and (ii) the second electrode to the common node through the second sampling capacitor, thereby producing the reference voltage at the common node;

charging the first sampling capacitor to a first voltage that represents a first voltage difference between the first electrode's voltage and the reference voltage at the common node; and charging the second sampling capacitor to a second voltage that represents a second voltage difference between the second electrode's voltage and the reference voltage at the common node.

12. The system of claim 11, wherein the stimulation circuit further comprises:

a first circuit component electrically coupled to the first sampling capacitor, the first circuit component being configured to generate a first signal based on the first voltage across the first sampling capacitor; and a second circuit component electrically coupled to the second sampling capacitor, the second circuit component being configured to generate a second signal based on the second voltage across the second sampling capacitor.

13. The system of claim 12, wherein the first circuit component is configured to supply the first signal to the first current source and the second circuit component is configured to supply the second signal to the second current source.

14. The system of claim 13, wherein:

the first current source is configured to receive the first signal and adjust the one or more characteristics based on the first signal; and the second current source is configured to receive the second signal and adjust the one or more characteristics based on the second signal.

15. The system of claim 14, wherein:

the first current source includes a first transistor with a first gate; and the first circuit component is configured to supply the first signal to the first gate of the first transistor.

16. The system of claim 12, wherein the first circuit component comprises a voltage-to-current converter, a processor, or a comparator.

17. The system of claim 16, wherein the first circuit component is the voltage-to-current converter, and wherein the first signal is a first current that is proportional to the first voltage across the first sampling capacitor.

18. The system of claim 8, wherein the stimulation circuit is configured to generate at least one of the stimulation currents based on a difference between the reference voltage and a voltage at a first electrode within the set of electrodes.

19. A neural stimulation apparatus, comprising:

a first current source coupled to a set of electrodes, the set of electrodes being configured to be coupled to a nerve fiber to implement a neural stimulation procedure;

a second current source coupled to the set of electrodes;

a stimulation circuit electrically coupled to the first current source, the second current source, and the set of electrodes, the stimulation circuit being configured to:

apply stimulation currents from the first current source through the set of electrodes to the nerve fiber during a stimulation phase of a treatment cycle of the neural stimulation procedure;

apply recovery currents from the second current source through the set of electrodes to the nerve fibers during a recovery phase that is subsequent to the stimulation phase in the treatment cycle, the recovery currents having opposite polarities to the respective stimulation currents;

generate a first signal based on a first voltage across a first sampling capacitor of the stimulation circuit, the first voltage across the first sampling capacitor being dependent on a reference voltage that is derived from voltages on the set of electrodes;

generate a second signal based on a second voltage across a second sampling capacitor of the stimulation circuit, the second voltage across the second sampling capacitor being dependent on the reference voltage;

transmit the first signal to the first current source or the second signal to the second current source for adjusting one or more characteristics of the stimulation currents or the recovery currents, respectively; and apply the stimulation currents or the recovery currents with the adjusted one or more characteristics through the set of electrodes to the nerve fiber during a subsequent treatment cycle of the neural stimulation procedure.

* * * * *